(12) United States Patent
Araki et al.

(10) Patent No.: US 10,422,774 B2
(45) Date of Patent: Sep. 24, 2019

(54) SYSTEM AND METHOD FOR DETECTING ABNORMALITY OF ROTATING MACHINES

(71) Applicant: Kobe Steel, Ltd., Hyogo (JP)

(72) Inventors: Kaname Araki, Kobe (JP); Eiji Takahashi, Kobe (JP); Shugo Takaki, Takasago (JP); Masato Hayashi, Takasago (JP)

(73) Assignee: Kobe Steel, Ltd., Hyogo (JP)

( * ) Notice: Subject to any disclaimer, the term of this patent is extended or adjusted under 35 U.S.C. 154(b) by 339 days.

(21) Appl. No.: 15/392,592

(22) Filed: Dec. 28, 2016

(65) Prior Publication Data
US 2017/0227505 A1      Aug. 10, 2017

(30) Foreign Application Priority Data

Feb. 10, 2016   (JP) .................................. 2016-023882

(51) Int. Cl.
  *F01D 21/00*   (2006.01)
  *F04D 27/00*   (2006.01)
  (Continued)

(52) U.S. Cl.
  CPC ........... *G01N 29/46* (2013.01); *F01D 21/003* (2013.01); *F04D 27/001* (2013.01); *G01M 15/14* (2013.01);
  (Continued)

(58) Field of Classification Search
  CPC ....... F04D 27/00; F04D 27/003; G01N 29/46; G01M 15/14
  (Continued)

(56) References Cited

U.S. PATENT DOCUMENTS 4,425,798 A * 1/1984 Nagai .................... G01H 1/003
                                                        702/77
5,965,819 A * 10/1999 Piety ...................... G01N 29/44
                                                        702/56
(Continued)

FOREIGN PATENT DOCUMENTS

CN          201637483 U      11/2010
CN          103688144 A       3/2014
(Continued)

OTHER PUBLICATIONS

The extended European Search Report issued by the European Patent Office dated Jul. 11, 2017, which corresponds to EP16207234.2 and is related to U.S. Appl. No. 15/392,592.

*Primary Examiner* — John E Breene
*Assistant Examiner* — Jeffrey P Aiello
(74) *Attorney, Agent, or Firm* — Studebaker & Brackett PC

(57) ABSTRACT

A system for detecting an abnormality of rotating machines includes two or more devices for detecting an abnormality and a computer. The respective devices include a sensor for detecting vibration of the respective rotating machines and generating signals indicative of the vibration, and a transmitting unit for transmitting the signals to the computer. The computer includes a sampler for sampling the signals with a sampling frequency and outputting, at a time at intervals of a predetermined period, a plurality of the data detected and sampled within the predetermined period, a storage for storing the data, a frequency analyzer for analyzing the frequencies of the data, a determination unit for determining whether the machines have an abnormality based on the results of the frequency analysis, and a display unit for displaying, in chronological order and in real time, the (Continued)

results of the frequency analysis and displaying the results of the determination.

18 Claims, 5 Drawing Sheets

(51) Int. Cl.
    *G01M 15/14*     (2006.01)
    *G01N 29/46*     (2006.01)
    *G01N 29/14*     (2006.01)
    *G01N 29/44*     (2006.01)

(52) U.S. Cl.
    CPC ......... *G01N 29/14* (2013.01); *G01N 29/4427* (2013.01)

(58) Field of Classification Search
    USPC ............................................ 702/34, 56, 182
    See application file for complete search history.

(56) References Cited

U.S. PATENT DOCUMENTS

| | | | | |
|---|---|---|---|---|
| 6,452,416 B1* | 9/2002 | Kaneda | ................ | G01R 31/343 219/69.18 |
| 2005/0222506 A1* | 10/2005 | Takimoto | ................ | A61B 8/06 600/455 |
| 2010/0116060 A1* | 5/2010 | Murayama | ............. | G01H 1/003 73/593 |
| 2011/0150062 A1* | 6/2011 | Inadomaru | ........... | G01R 23/173 375/224 |
| 2011/0209546 A1* | 9/2011 | Seuthe | ............... | B23Q 17/0976 73/579 |
| 2013/0167653 A1* | 7/2013 | Seuthe | ................... | B29C 45/76 73/861.18 |
| 2014/0142872 A1* | 5/2014 | Hedin | .................... | G01H 1/003 702/56 |
| 2014/0324367 A1* | 10/2014 | Garvey, III | ............ | G01D 18/00 702/56 |
| 2015/0343120 A1* | 12/2015 | Yokoi | ................. | A61M 1/0013 604/318 |
| 2018/0059656 A1* | 3/2018 | Hiruta | .................... | G05B 23/02 |

FOREIGN PATENT DOCUMENTS

| | | |
|---|---|---|
| JP | S63-150633 A | 6/1988 |
| JP | 08-166330 A | 6/1996 |
| JP | 2001-125634 A | 5/2001 |
| JP | 2010-234422 A | 10/2010 |
| WO | 2013/009258 A1 | 1/2013 |

\* cited by examiner

SYSTEM AND METHOD FOR DETECTING ABNORMALITY OF ROTATING MACHINES

FIELD OF THE INVENTION

The present invention relates to a system and a method for suitably detecting an abnormality of a rotating machine such as, for example, an abnormality of a rotor.

DESCRIPTION OF THE RELATED ART

During the operation of rotating machines such as turbines and compressors, rotors usually rotate at high speed. Later detection of an abnormality such as damage of the rotors, for example, may lead to increased severity of the abnormality. To make matters worse, the abnormality may result in shutdown of the rotating machines. Thus, it is desirable to early detect and notify such abnormality of rotating machines.

For example, a device for diagnosing abnormal slide, described in JP 8-166330, uses an AE (acoustic emission) sensor to detect an AE signal from a rotating machine; analyzes the frequency of the detected AE signal to determine the presence, location, and degree of abnormal slide; and displays the result of the determination.

Problems to be Solved by the Invention

If an operator can comprehend the operating states of a rotating machine at respective times, the operator can recognize a change in operation states of the rotating machine over time, thereby allowing earlier detection of an abnormality of the rotating machine. Although the conventional device described in JP 8-166330 displays the results of determination of the presence, location, and degree of abnormal slide, the device does not display trends in the results over time. Thus, the conventional device can identify, for example, the presence of an abnormality of a rotating machine but is difficult to early detect the abnormality.

The present invention has been developed in view of the foregoing. It is an object of the present invention to provide a system and a method for detecting an abnormality of a rotating machine, the system and the method being able to early detect an abnormality of a rotating machine

Means of Solving the Problems

A first aspect of the present invention is a system for detecting an abnormality of rotating machines, the system including two or more devices for detecting an abnormality and a computer, wherein the two or more devices detect an abnormality of two or more rotating machines to which the devices are allocated respectively, wherein the two or more devices individually include a sensor for detecting vibration of rotating machines to which the devices are allocated and generating a signal indicative of the detected vibration and a transmitting unit for transmitting, to the computer, the signal generated by the sensor, and wherein the computer includes a sampler for sampling and detecting, with a predetermined sampling frequency, the signal that is transmitted by the transmitting units of the respective two or more devices and that are indicative of the vibration and outputting, at a time at intervals of a predetermined period, a plurality of the sampled data detected within the predetermined period, a storage for storing the plurality of the sampled data that are outputted by the sampler and that correspond to the respective two or more rotating machines, a frequency analyzer for analyzing frequencies of the plurality of the sampled data that are outputted by the sampler and that correspond to the respective two or more rotating machines, an abnormality determination unit for determining whether the respective two or more rotating machines have an abnormality based on the results of the frequency analysis by the frequency analyzer, the results corresponding to the respective two or more rotating machines, and a display unit for displaying, in chronological order and in real time, the results of the frequency analysis, the results corresponding to the respective two or more rotating machines and for displaying the result of the determination.

The sampler outputs, at a time at intervals of a predetermined period, a plurality of the sampled data detected within the predetermined period. The sampler may output, at a time at intervals of a predetermined period, all of a plurality of the sampled data detected within the predetermined period or may output, at a time, part of the plurality of the sampled data.

The system for detecting an abnormality of rotating machines according to the first aspect of the present invention displays, in chronological order and in real time, the results of frequency analysis of the sampled data created by sampling and detecting vibration of the rotating machines. In other words, the system displays, substantially in real time, the operating states of the rotating machines at respective times, which allows an operator to recognize a change in operation states of the rotating machines over time. Thus, the system for detecting an abnormality of rotating machines according to the first aspect of the present invention can early detect an abnormality of the rotating machines.

The system for detecting an abnormality of rotating machines according to the first aspect of the present invention displays, on the single display unit, the results of the frequency analysis and the results of the abnormality determination for the respective two or more rotating machines, which allows collective control of detection of an abnormality of the respective two or more rotating machines. Thus, the system for detecting an abnormality of rotating machines according to the first aspect of the present invention allows a reduction in the number of people who manage the process of detecting an abnormality of two or more rotating machines.

In the system for detecting an abnormality of rotating machines, the frequency analyzer preferably analyzes frequencies of the plurality of the sampled data by fast Fourier transform and outputs amplitude data corresponding to the respective frequencies.

In the system for detecting an abnormality of rotating machines in the preferred implementation, use of fast Fourier transform allows suitable real-time display of the results of the frequency analysis.

In the system for detecting an abnormality of rotating machines, the display unit displays the results of the frequency analysis in two dimensions: the frequency dimension and the amplitude dimension. More preferably, the display unit displays the results of the frequency analysis at respective times in chronological order, in three dimensions, and in real time.

In the system for detecting an abnormality of rotating machines in the preferred implementation, the display unit displays the results of the frequency analysis of the sampled data in chronological order, in real time, and in three dimensions: the frequency dimension, the amplitude dimension (the amplitude dimension indicating amplitudes corresponding to respective frequencies), and time dimension, which allows an operator to readily visually recognize a change in operation states of the rotating machines over time.

In the system for detecting an abnormality of rotating machines, the frequency analyzer initiates the frequency analysis when the frequency analyzer has received the plurality of the sampled data from the detecting unit. Preferably, the analysis period from the initiation of the frequency analysis to the end of the frequency analysis is shorter than the predetermined period described above.

In the system for detecting an abnormality of rotating machines in the preferred implementation, the frequency analyzer can complete, within the predetermined period, the frequency analysis of all of the plurality of the sampled data received at the beginning of the predetermined period.

In the system for detecting an abnormality of rotating machines, the storage initiates storage of the plurality of the sampled data and the results of the frequency analysis when the storage has received the plurality of the sampled data from the detecting unit. Preferably, the storage period from the initiation of storage of the plurality of the sampled data to the end of the storage is shorter than the predetermined period.

In the system for detecting an abnormality of rotating machines in the preferred implementation, the storage can initiate storage of the plurality of the sampled data and the results of the frequency analysis when the storage has received the data. The system for detecting an abnormality of rotating machines can store, to the storage within the predetermined period, all of the plurality of the sampled data received at the beginning of the predetermined period.

Preferably, the system for detecting an abnormality of rotating machines further includes a termination instruction input unit for receiving an instruction to terminate detection of the abnormality. When the termination instruction input unit has received the instruction, the frequency analyzer preferably reads all of the plurality of the sampled data stored in the storage, performs the frequency analysis, and stores the results of the frequency analysis in chronological order in the storage.

In the preferred implementation, the frequency analyzer stores the results of the frequency analysis in chronological order in the storage upon terminating detection of the abnormality, which can reduce the processing load for the storage process, for example via a controller, compared with a case in which the results of the frequency analysis are stored during the frequency analysis.

In the system for detecting an abnormality of rotating machines, the frequency analyzer is functionally configured in a processor by executing a predetermined frequency-analysis-program. Preferably, the frequency analyzer is functionally configured in the processor upon initiating the frequency analysis, while the frequency analyzer is cleared from the processor upon terminating the frequency analysis.

In the system for detecting an abnormality of rotating machines in the preferred implementation, a plurality of frequency analyzers can be functionally configured in parallel. As the frequency analyzers are configured when necessary, the system for detecting an abnormality of rotating machines only needs to control the frequency analyzers that are functionally configured in the processor when necessary, which can reduce the processing load of the processor, compared with a case in which a predetermined number of frequency analyzers are functionally pre-configured.

A second aspect of the present invention is a method for detecting an abnormality of two or more rotating machines by using two or more devices for detecting an abnormality of the two or more rotating machines to which the devices are allocated respectively, the method including a step of detecting vibration of the rotating machines to which the devices are allocated and generating signals indicative of the detected vibration by the respective two or more devices, a step of transmitting, by the respective two or more devices, the signals generated in the generation step, a step of sampling and detecting, with a predetermined sampling frequency, the signals that are transmitted in the transmission step by the respective two or more devices and that are indicative of the vibration and outputting, at a time at intervals of a predetermined period, a plurality of the sampled data detected within the predetermined period, a step of storing the plurality of the sampled data that are outputted in the sampling step and that correspond to the respective two or more rotating machines, a step of analyzing frequencies of the plurality of the sampled data that are outputted in the sampling step and that correspond to the respective two or more rotating machines, a step of determining whether the respective two or more rotating machines have an abnormality based on the results of the frequency analysis in the frequency analysis step, the results corresponding to the respective two or more rotating machines, and a step of displaying, in chronological order and in real time, the results of the frequency analysis, the results corresponding to the respective two or more rotating machines and of displaying the result of the determination.

The second aspect of the present invention has the same effects as the first aspect of the present invention.

Effects of the Invention

The present invention allows early detection of an abnormality of a rotating machine.

DESCRIPTION OF THE EMBODIMENTS

Figure 1:
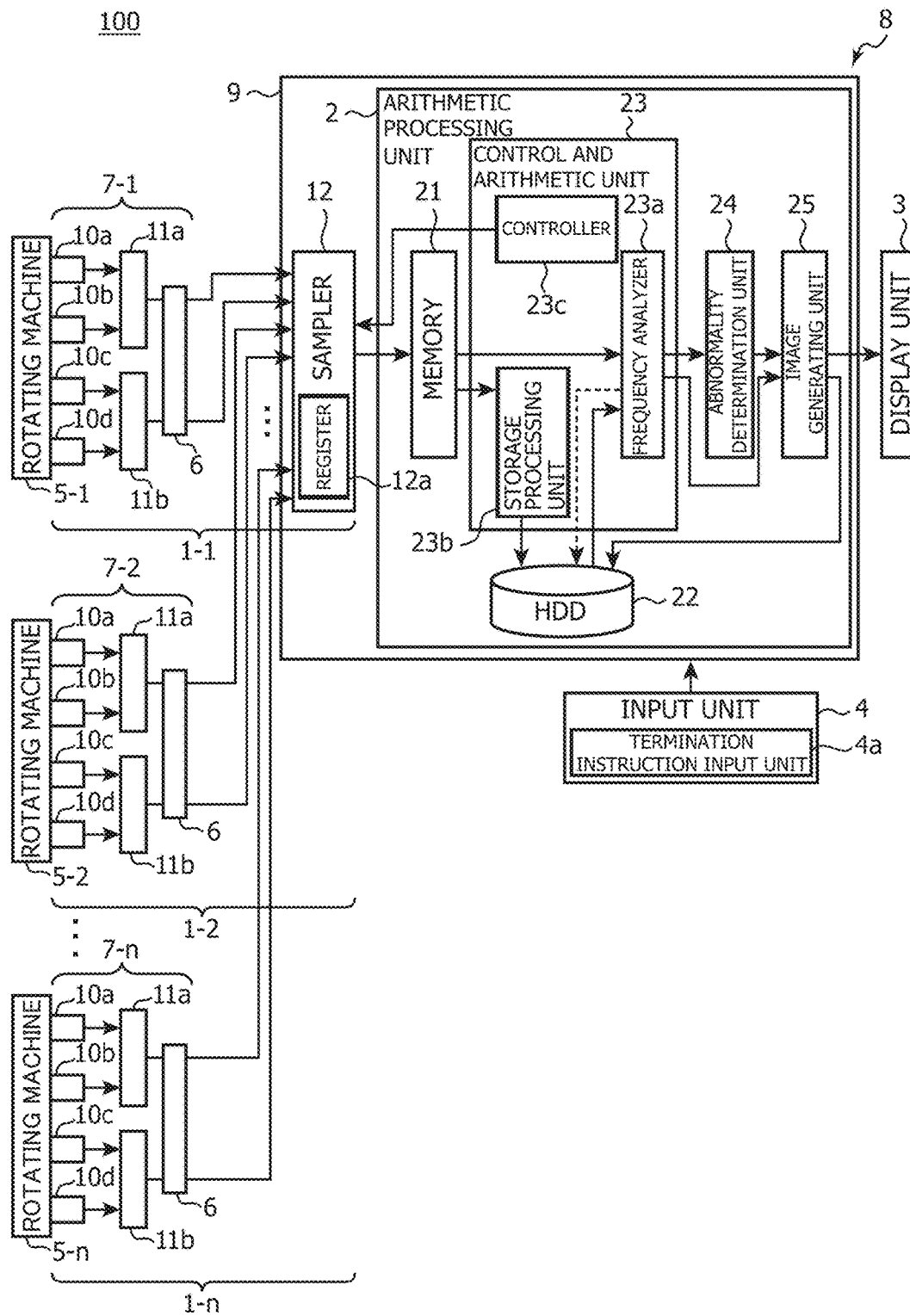
FIG. 1 is a block diagram illustrating an exemplary configuration of a system for detecting an abnormality of rotating machines according to an embodiment of the present invention.

Now, an embodiment of the present invention will be described with reference to the drawings. In the drawings, like references designate like elements, the description of which is omitted if unnecessary. As used herein, a numeral with no letter suffix indicates a generic element, while a numeral with a letter suffix indicates an individual element.

FIG. 1 is a block diagram illustrating an exemplary configuration of a system 100 for detecting an abnormality of rotating machines (hereinafter also simply referred to as "system for detecting an abnormality") according to an embodiment of the present invention. The system 100 for detecting an abnormality controls an abnormality of respective n rotating machines 5-1 to 5-n by a single computer 8, wherein n is an integer of two or more. The rotating machines 5-1 to 5-n may be collectively referred to as "rotating machines 5". For example, the n rotating machines 5 may be disposed in a single line, or each of the n rotating machines 5 may be disposed in each of n lines.

As illustrated in FIG. 1, the system 100 for detecting an abnormality includes, for example, n detecting units 1-1 to 1-n, an arithmetic processing unit 2, a display unit 3, and an input unit 4. The detecting units 1-1 to 1-n may be collectively referred to as "detecting units 1". The detecting units 1 are connected to the arithmetic processing unit 2, which is connected to the display unit 3. The input unit 4 is connected to the arithmetic processing unit 2.

The computer 8 is constituted by the arithmetic processing unit 2, a sampler 12, the display unit 3, and the input unit 4. A computer unit 9 is constituted by the arithmetic processing unit 2 and the sampler 12.

The respective detecting units 1-1 to 1-n are allocated to the respective n rotating machines 5-1 to 5-n. In particular, the detecting unit 1-1 is used to detect an abnormality of the rotating machine 5-1, the detecting unit 1-2 is used to detect an abnormality of the rotating machine 5-2, and the detecting unit 1-n is used to detect an abnormality of the rotating machine 5-n. The detecting units 1-1 to 1-n have the same configuration. The detecting units 1-1 to 1-n share the sampler 12. When the system 100 for detecting an abnormality of rotating machines includes a lot of the detecting units 1, the system 100 includes a plurality of the samplers 12, and the n detecting units 1-1 to 1-n are divided into a plurality of groups. The detecting units 1 in each of the groups may be allocated to one of the samplers 12. This allows prevention of latency in processing by the samplers 12 even when the system 100 includes a lot of the detecting units 1.

The detecting units 1 sample and detect vibration of the rotating machines 5 to be inspected with a predetermined sampling frequency, and outputs, to the arithmetic processing unit 2 at a time at intervals of a predetermined period, all of a plurality of the sampled data detected within the predetermined period. The detecting units 1 include, for example, sensors 10 (10a to 10d), amplifiers 11 (11a and 11b), a transmitting unit 6, and the sampler 12. The sensors 10 are connected to the amplifiers 11, which are connected to the transmitting unit 6. Then, the transmitting unit 6 is connected to the sampler 12, which is connected to the arithmetic processing unit 2.

The sensors 10 detect vibration of the rotating machines 5 to be inspected. For example, the sensors 10 are an electro-mechanical energy converting element that contains a material such as piezoceramics and that converts vibrational mechanical energy to electrical energy. More particularly, the sensors 10 are, for example, AE (acoustic emission) sensors, acceleration sensors or the like. One or more sensors 10 may be used. In the embodiment, two AE sensors 10a and 10b and two acceleration sensors 10c and 10d are used. As illustrated in FIG. 1, the AE sensors 10a and 10b and the acceleration sensors 10c and 10d are attached to the body of the rotating machines 5 such as turbines and compressors. For example, when the rotating machines 5 are compressors, the AE sensors 10a and 10b detect an abnormality, such as, contact between two rotors that are usually spaced from each other, by detecting AE waves due to the abnormality. The acceleration sensors 10c and 10d detect the vibration acceleration of the rotating machines 5 due to the abnormality.

The amplifiers 11 amplify each small detected signal outputted by the sensors 10. The number of the amplifiers 11 depends on the number of the sensors 10. In the embodiment, two amplifiers 11a and 11b are used. The amplifier 11a is connected to the AE sensors 10a and 10b. The amplifier 11b is connected to the acceleration sensors 10c and 10d. The amplifier 11a individually amplifies each signal outputted by the AE sensors 10a and 10b and individually outputs each amplified signal. The amplifier 11b individually amplifies each signal outputted by the acceleration sensors 10c and 10d and individually outputs each amplified signal. The transmitting unit 6 transmits, to the sampler 12, the signals amplified by the amplifiers 11a and 11b.

The sampler 12 samples the vibration of the rotating machines 5 with a predetermined sampling frequency and outputs all of the plurality of the sampled data to the arithmetic processing unit 2. All of the plurality of the sampled data are outputted at a time by the sampler 12, as instructed by the arithmetic processing unit 2. For example, in the embodiment, the sampler 12, which includes, for example, a register 12a, individually samples respective signals that are, for example, detected by the AE sensors 10a and 10b and that are individually outputted by the amplifier 11a with a sampling frequency of 1 MHz at the same timing; A/D-converts the signals; and stores the signals in the register 12a. On the other hand, the sampler samples respective signals that are detected by the acceleration sensors 10c and 10d and individually outputted by the amplifier 11b with a sampling frequency of 20 kHz at the same timing; A/D-converts the signals; and stores the signals in the register 12a. Therefore, all of the sampled data Da are stored in the register 12a. The sampler 12 outputs, to the arithmetic processing unit 2 at a time at intervals of a predetermined period as instructed by the arithmetic processing unit 2, all of the sampled data Da that are detected within the predetermined period and that are stored in the register 12a. The register 12a assembles the signals detected by the AE sensors 10a and 10b, amplified by the amplifier 11a, sampled, and A/D-converted (hereinafter also referred to as "AE data") into a single electronic file with the arrival of every predetermined number of the signals, for example every 102,400 signals, and outputs the signals at a time to the arithmetic processing unit 2. The AE data are outputted to the arithmetic processing unit 2 at intervals of about 0.1 sec (102,400/1 MHz≈about 0.1 sec). For the AE data, the predetermined period is about 0.1 sec in the embodiment. The register 12a also assembles the signals outputted by the acceleration sensors 10c and 10d, amplified by the amplifier 11b, sampled, and A/D-converted (hereinafter also referred to as "acceleration data") into a single electronic file with the arrival of every predetermined number of signals, for example, every 65,536 signals and outputs the signals at a time to the arithmetic processing unit 2. The acceleration data are outputted to the arithmetic processing unit 2 at intervals of about 3.3 sec (65,536/20 kHz≈about 3.3 sec). For the acceleration data, the predetermined period is about 3.3 sec in the embodiment.

In the detecting units 1, the sensors 10 detect vibration of the rotating machines 5 and output analog signals indicative of the vibration to the amplifiers 11. Then, the amplifiers 11 amplify the signals, which are then inputted to the sampler 12 via the transmitting unit 6. The sampler 12 samples and digitizes the inputted signals before outputting the signals to the arithmetic processing unit 2 at a predetermined timing.

As described above, the respective n detecting units 1-1 to 1-n sample and detect vibration of the respective rotating machines 5-1 to 5-n to which the detecting units are allocated with a predetermined sampling frequency, and output, at a time at intervals of a predetermined period, all of a plurality of the sampled data detected within the predetermined period. Instead of outputting all of the plurality of the sampled data at a time, the sampler 12 may output a part of the plurality of the sampled data at a time. More particularly, instead of outputting, for example, 102,400 sampled signals at a time, the sampler 12 may output part of 102,400 sampled signals (for example, 51,200 sampled signals) at a time.

The detecting units 1 are constituted by the sensors 10, the amplifiers 11, the transmitting unit 6, and the sampler 12, which is disposed in the computer unit 9 and is separated from the sensors 10, the amplifiers 11, and the transmitting unit 6. In this regards, the sensors 10, the amplifiers 11, the transmitting unit 6, and the sampler 12 can be described as follows.

The sensors 10, the amplifiers 11, and the transmitting unit 6 constitute a device 7 for detecting an abnormality. The system 100 includes the n devices 7 for detecting an abnormality (devices 7-1 to 7-n for detecting an abnormality). The devices 7-1 to 7-n may be collectively referred to as devices 7 for detecting an abnormality. The respective devices 7-1 to 7-n are allocated to the respective n rotating machines 5-1 to 5-n. In particular, the device 7-1 for detecting an abnormality is used to detect an abnormality of the rotating machine 5-1, the device 7-2 for detecting an abnormality is used to detect an abnormality of the rotating machine 5-2, and the device 7-n for detecting an abnormality is used to detect an abnormality of the rotating machine 5-n. The devices 7-1 to 7-n for detecting an abnormality have the same configuration.

The sensors 10 detect vibration of the rotating machines 5 to which the sensors are allocated and generate signals indicative of the detected vibration. The amplifiers 11 amplify the signals generated by the sensors 10. The transmitting unit 6 is a transmitter (transmitting circuit) that transmits the signals amplified by the amplifiers 11 to the computer 8 by cable or wirelessly.

The sampler 12 samples and detects, with a predetermined sampling frequency, the signals that are transmitted by the respective transmitting units 6 of the n devices 7-1 to 7-n for detecting an abnormality and that are indicative of the vibration and outputs, at a time at intervals of a predetermined period, a plurality of the sampled data detected within the predetermined period.

Now, in placed of the detecting units 1, the devices 7 for detecting an abnormality and the sampler 12 will be used for description.

The arithmetic processing unit 2 analyzes frequencies of the sampled data Da sampled and detected by the sampler 12 and generates image data for displaying, in chronological order and in real time, the results of the frequency analysis of the signals sampled and detected within the predetermined period. The arithmetic processing unit 2 includes, for example, a memory 21, a HDD (hard disk drive) 22, a control and arithmetic unit 23, an abnormality determination unit 24, and an image generating unit 25. The memory 21 and the HDD 22 are examples of a storage for storing the sampled data Da outputted by the sampler 12. The sampler 12 is connected to the memory 21 and the control and arithmetic unit 23. The memory 21 is connected to the control and arithmetic unit 23. The control and arithmetic unit 23 is connected to the HDD 22, the abnormality determination unit 24, and the image generating unit 25. The abnormality determination unit 24 is connected to the image generating unit 25. The image generating unit 25 is connected to each of the display unit 3 and the the HDD 22. The control and arithmetic unit 23 provides an output to the abnormality determination unit 24 and the image generating unit 25. In particular, the control and arithmetic unit 23 provides an output via the abnormality determination unit 24 to the image generating unit 25. The image generating unit 25 provides an output to the display unit 3. The HDD 22 receives image data from the image generating unit 25.

The memory 21 temporarily stores all of the sampled data Da outputted by the sampler 12. The control and arithmetic unit 23 reads the sampled data Da stored in the memory 21. The memory 21 allows all of the sampled data Da outputted at a time by the sampler 12 to be held. Then, all of the sampled data Da can be stored on the the HDD 22, and a frequency analyzer 23a can use all of the sampled data Da to analyze the frequency.

The HDD 22 stores the sampled data Da outputted by the sampler 12. In the embodiment, for example, a storage processing unit 23b, which is described below, stores, on the HDD 22, all of the sampled data Da stored in the memory 21. In the embodiment, the storage processing unit 23b initiates storage of the sampled data Da on the HDD 22 when, for example, the unit 23b has received the sampled data Da from the sampler 12.

In this manner, the memory 21 and the HDD 22 store a plurality of the sampled data that correspond to the respective n rotating machines 5-1 to 5-n and that are outputted by the sampler 12.

The control and arithmetic unit 23 provides overall control of the sampler 12, the arithmetic processing unit 2, the display unit 3, and the input unit 4 and performs various arithmetical operations. The control and arithmetic unit 23 includes, for example, a processor such as a CPU (central processing unit), a ROM (read only memory), a RAM (random access memory) with the memory 21 functionally configured therewith, and their peripheral circuits. The control and arithmetic unit 23 includes, for example, the frequency analyzer 23a, the storage processing unit 23b, and a controller 23c. In the embodiment, the control and arithmetic unit 23 executes an abnormality detection program for detecting an abnormality, the program being stored in the ROM, so that the frequency analyzer 23a, the storage processing unit 23b, and the controller 23c are functionally configured in the control and arithmetic unit 23. In the control and arithmetic unit 23, a plurality of the frequency analyzers 23a can be functionally configured in parallel so that the plurality of the frequency analyzers 23a can be executed in parallel. In the embodiment, upon initiating the frequency analysis, the frequency analyzer 23a and the storage processing unit 23b are functionally configured in the control and arithmetic unit 23, for example, simultaneously, while upon completing the frequency analysis, the frequency analyzer 23a and the storage processing unit 23b are cleared from the control and arithmetic unit 23. The frequency analyzer 23a is connected to the memory 21 and the HDD 22 and provides an output to the abnormality determination unit 24 and the image generating unit 25. The storage processing unit 23b is connected to the memory 21 and the HDD 22.

The frequency analyzer 23a analyzes the frequencies of the sampled data Da outputted by the sampler 12. In particular, the frequency analyzer 23a analyzes the frequencies of a plurality of the sampled data Da that are outputted by the sampler 12 and that correspond to the respective n rotating machines 5-1 to 5-n and generates the results of the frequency analysis. In the embodiment, for example, the frequency analyzer 23a analyzes the frequencies of the sampled data Da by fast Fourier transform (FFT) and outputs frequency characteristics of the sampled data Da, i.e., amplitude data corresponding to the respective frequencies.

The frequency analyzer 23a performs fast Fourier transform of the AE data, for example, every 4,096 signals. As described above, the AE data are inputted to the memory 21 at a time, every 102,400 signals, and thus fast Fourier transform of the AE data are performed 25 times (10,2400/4,096=25) within the predetermined period (about 0.1 sec). The frequency analyzer 23a uses, for example, the average values of the results of 25 times fast Fourier transform obtained within the predetermined period as the results of the fast Fourier transform in the predetermined period. The fast Fourier transform of the acceleration data is performed, for example, every 65,536 signals. As described above, the acceleration data are inputted to the memory 21 at a time, every 65,536 signals, and thus the fast Fourier transform of the acceleration data are performed once within the predetermined period (about 3.3 sec). When the termination instruction input unit (input unit) 4 has received an instruction to terminate detection of an abnormality from an operator who operates the system 100 for detecting an abnormality, the frequency analyzer 23a reads the sampled data Da at all of the time points from the HDD to analyze the frequencies of the data and then outputs the results of the frequency analysis to the image generating unit 25.

The storage processing unit 23b stores, on the HDD 22, the sampled data Da read from the memory 21. The controller 23c provides overall control or the like of the arithmetic processing unit 2. The controller 23c outputs an instruction to the sampler 12 to output all of the sampled data Da at a time. In the embodiment, the instruction to output the data at a time is outputted by the controller 23c to the sampler 12 at intervals of the predetermined period. The controller 23c outputs an instruction to the sampler 12 to start sampling and A/D conversion.

The abnormality determination unit 24 uses the results of the frequency analysis by the frequency analyzer 23a to determine the presence of an abnormality of, for example, rotors or the like of the rotating machines 5. The abnormality determination unit 24 extracts a characteristic value such as, for example, the maximum value, average, or standard deviation of the amplitude values or the median or standard deviation of the frequencies from the results of the frequency analysis and determines whether the characteristic value meets a predetermined criterion by comparing the characteristic value with a threshold predetermined based on, for example, a past abnormality data, an experimental result, a simulation result or the like to determine the presence of an abnormality of, for example, the rotors or the like. When the rotating machines 5 are compressors, the abnormality determination unit 24 outputs, to the image generating unit 25, an alarm message, for example, that indicates suspected contact between the two rotors as the result of the abnormality determination.

Figure 2:
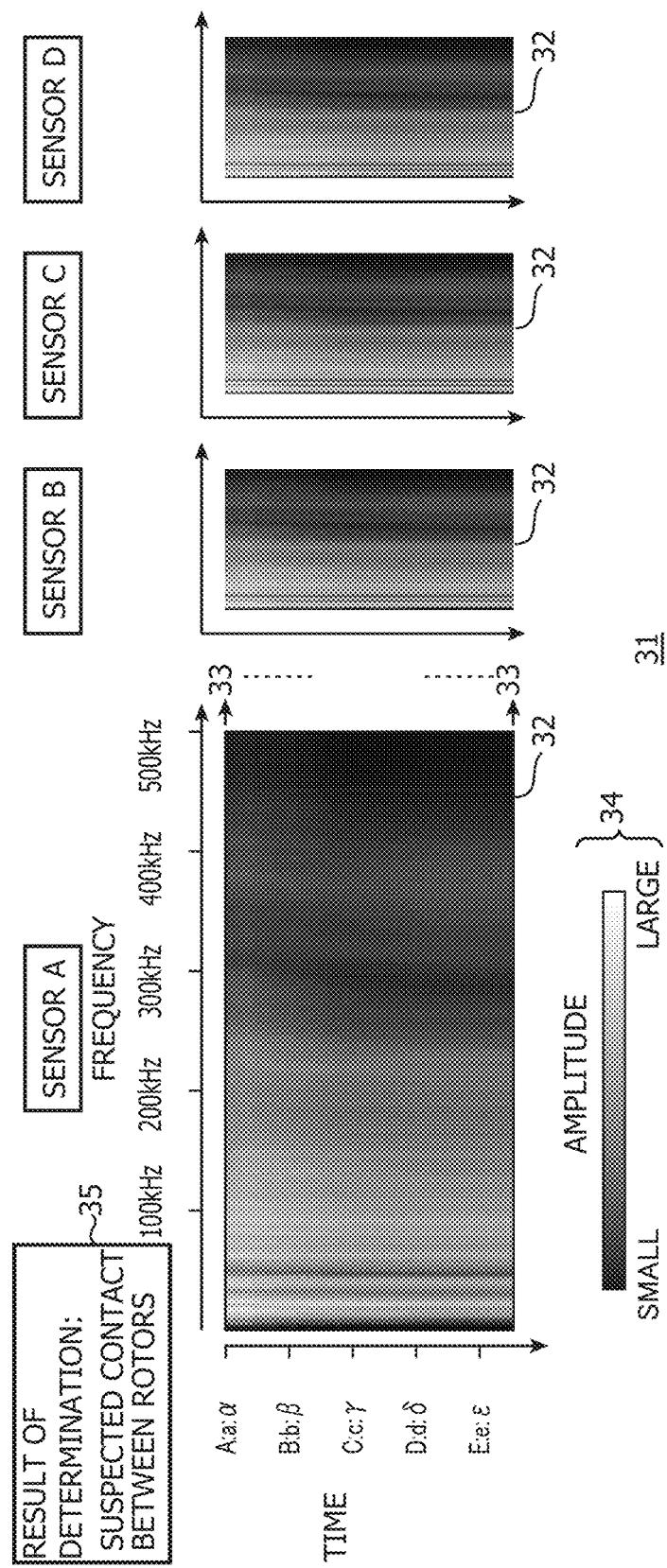
FIG. 2 is an exemplary image displayed on a display unit according to an embodiment of the present invention.

The image generating unit 25 generates image data to be displayed on the display unit 3. The image generating unit 25 generates, for example, image data showing the results of the frequency analysis in chronological order and in real time. The image data show the results of the frequency analysis in, for example, two dimensions: the frequency dimension and the amplitude dimension. The image data also shows the two dimensional results (the results of the frequency analysis) at the most current time point and previous time points in chronological order, thereby displaying the data in real time and in three dimensions (hereinafter such data is also referred to as "three-dimensional image data"). FIG. 2 illustrates an exemplary image displayed on a display screen 31 of the display unit 3. The display screen 31 displays partial images 32 (images of the three-dimensional image data) from each of the sensors (in FIG. 2, Sensor A, Sensor B, Sensor C, and Sensor D respectively corresponding to the AE sensor 10a, the AE sensor 10b, the acceleration sensor 10c, and the acceleration sensor 10d), the display screen 31 showing the result of the frequency analysis at the most current time point (E:e:ε in FIG. 2) and the results of the frequency analysis at previous time points (from A:a:α to E:e:ε in FIG. 2) in chronological order, in three dimensions, and in real time. The display screen 31 also has a result-displaying portion 35 on which the result of the determination (such as an alarm message) is displayed at a predetermined location, and a legend image 34, which is described below. The partial images 32 show the results of the frequency analysis, where time is taken along the ordinate, and frequency is taken along the abscissa. For convenience of description, the image of Sensor A is larger than the images of Sensors B-D in FIG. 2. The partial images 32 of the respective sensors are a planar image constituted by, for example, band partial images 33 that are arranged side by side in chronological order and that show the data in two dimensions: the frequency dimension and the amplitude dimension. In FIG. 2, the oldest amplitude data (two-dimensional band partial image 33) is deleted from the partial images 32, and the partial images 33 at the remaining time points are scrolled by the length for the deleted data. The latest partial image 33 at the most current time point is added at the bottom of the partial images 32.

In the embodiment, the amplitude data corresponding to the respective frequencies are shown, for example, using white and various shades of gray. The partial images 33 are, for example, constituted by a plurality of pixels of white or various shades of gray in the frequency dimension depending on the amplitude levels and are displayed as a band of white and various shades of gray in the two dimensions. In FIG. 2, the relationship between the amplitude data and the shades is illustrated by the legend image 34 displayed on a predetermined location on the display screen 31.

The band partial images 33 displayed in the two dimensions are constituted by, for example, 2,048 pixels arranged in the direction of the frequency dimension. In particular, the partial images 33 represent amplitude values for 2,048 frequencies. If the frequency analyzer 23a outputs a result of frequency analysis of more than 2,048 frequencies, 2,048 frequencies are selected from the outputted frequencies in a predetermined extraction operation to generate a partial image 33. For example, if a result of frequency analysis of 4,096 frequencies is outputted, 2,048 frequencies are selected by, for example, comparing amplitude values of two adjacent frequencies and selecting the frequency that has a higher amplitude value so as to generate a band partial image 33 constituted by 2,048 pixels arranged in the direction of the frequency dimension. As described above, selection of frequencies having a higher amplitude value, i.e., indicating a more severe abnormality allows the system 100 for detecting an abnormality to more suitably detect an abnormality.

When the termination instruction input unit (input unit) 4 has received an instruction to terminate detection of an abnormality from an operator, the image generating unit 25 receives the results of analysis of frequencies (the amplitude data) at all of the time points from the frequency analyzer 23a and then generates three-dimensional image data that show the results of analysis of frequencies at all of the time points, as described above. Then, the three-dimensional image data are transferred to and stored on the HDD 22.

The display unit 3 receives the image data from the image generating unit 25 and displays the results of the frequency analysis by the frequency analyzer 23a in chronological order and in real time. In particular, the display unit 3 displays, in chronological order and in real time, the results of the frequency analysis, the results being generated by the frequency analyzer 23a and corresponding to the respective n rotating machines 5-1 to 5-n. A single result of the frequency analysis is generated for each of the n rotating machines 5-1 to 5-n, and thus the number of the results are n. Although the display screen 31 shows a single result of the frequency analysis (for example, a result of the frequency analysis for the rotating machine 5-1) in FIG. 2, the display screen 31 also contains n−1 results (not shown) of the frequency analysis (the results of the frequency analysis for the rotating machines 5-2 to 5-n).

The abnormality determination unit 24 determines whether the respective rotating machines 5-1 to 5-n have an abnormality, based on the results of the frequency analysis by the frequency analyzer 23a, the results corresponding to the respective n rotating machines 5-1 to 5-n. In particular, the determination unit 24 determines whether the rotating machine 5-1 has an abnormality based on the results of the frequency analysis for the rotating machine 5-1. The determination unit 24 determines whether the rotating machine 5-2 has an abnormality based on the results of the frequency analysis for the rotating machine 5-2. And the determination unit 24 determines whether the rotating machine 5-n has an abnormality based on the results of the frequency analysis for the rotating machine 5-n. The rotating machines 5-3 to 5-n−1 also determine similarly.

When the abnormality determination unit 24 has determined that the rotating machines 5 have an abnormality, the display unit 3 identifies the rotating machines 5 that have an abnormality and displays an indication of the abnormality (for example, an alarm message). The indication of the abnormality is displayed on, for example, the result-displaying portion 35 in FIG. 2. Although the display screen 31 includes a single result-displaying portion 35 (for example, a result-displaying portion for the rotating machine 5-1) in FIG. 2, the display screen 31 also includes n−1 result-displaying portions (not shown) (result-displaying portions for the respective rotating machines 5-2 to 5-n).

The input unit 4 is an input device such as a mouse or keyboard for inputting information to the arithmetic processing unit 2. The input unit 4 includes a termination instruction input unit 4a that receives an instruction to terminate detection of abnormality from an operator. The termination instruction input unit 4a may be a predetermined key on the keyboard or a predetermined field on the display unit 3 for receiving a termination instruction input (a termination instruction input button).

Figure 3:
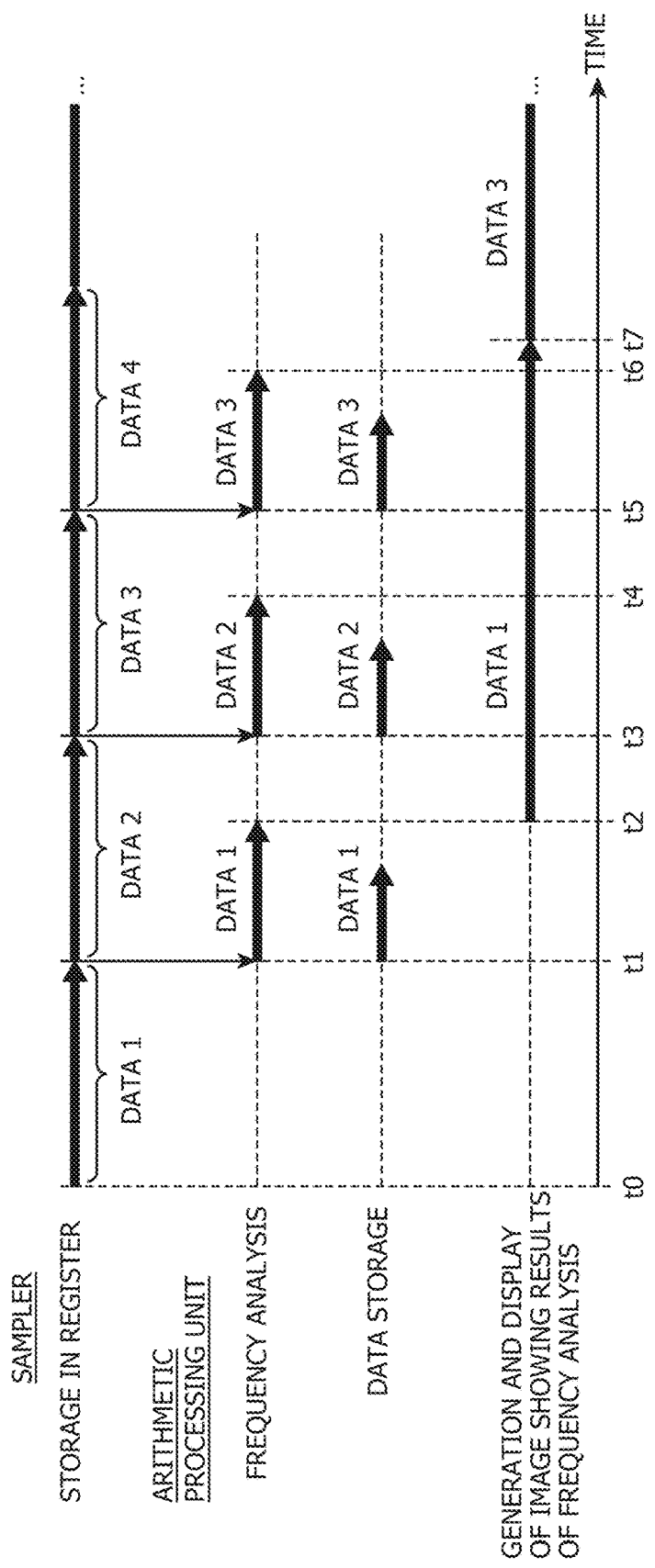
FIG. 3 is a timing chart illustrating the operation of a system for detecting an abnormality of rotating machines according to an embodiment of the present invention.

FIG. 3 is a timing chart illustrating the operation of the system 100 for detecting an abnormality of rotating machines according to the embodiment. FIG. 3 illustrates a timing chart of respective data about one of the rotating machines 5 (for example, the rotating machine 5-1). Respective data about the remaining rotating machines 5 (the rotating machines 5-2 to 5-n) are processed in the same manner as in FIG. 3.

In the timing chart, storage processing in the register 12a ("Storage in Register" in FIG. 3), frequency analysis processing by the frequency analyzer 23a ("Frequency Analysis" in FIG. 3), storage processing in the storage processing unit 23b ("Data Storage" in FIG. 3), and image generation processing by the image generating unit 25 and image display processing by the display unit 3 ("Generation and Display of Image Showing Results of Frequency Analysis" in FIG. 3) are taken along the ordinate. Time is taken along the abscissa. The data are stored in the register 12a at intervals of a predetermined period. Time t0 is the time at which the controller 23c instructs the sampler 12 to initiate sampling and A/D conversion. In the period from Time t0 to Time t1, at which the predetermined period has elapsed from Time t0, the sensors 10 (the AE sensors 10a and 10b and the acceleration sensors 10c and 10d) detect vibration of the rotating machines 5, the amplifiers 11 (11a and 11b) amplify signals indicative of the vibration, the sampler 12 samples and A/D-converts each signal, and the register 12a stores the sampled data Da (Data 1 in FIG. 3). At Time t1, all of a plurality of the sampled data Da (Data 1) detected within the predetermined period are stored in the register 12a, and then the sampled data Da (Data 1) stored are outputted by the register 12a to the memory 21 at a time, as instructed by the controller 23c. Similarly, in the period from Time t1 to Time t3, at which the predetermined period has elapsed, each detecting unit 1 detects the vibration, samples and A/D-converts the signals, and stores the sampled data Da (Data 2 in FIG. 3) in the register 12a again. At Time t3, all of the sampled data Da (Data 2) detected and within the predetermined period are stored in the register 12a, and then are outputted by the register 12a to the memory 21 at a time, as instructed by the controller 23c. In this manner, all of the plurality of the sampled data Da detected within the predetermined period are stored in the register 12a at intervals of the predetermined period, and all of the plurality of the sampled data Da are outputted at a time. Also after Time t3, data such as Data 3 are stored in the register 12a and outputted to the memory 21 in the same manner.

After Time t1, all of the sampled data Da (Data 1) outputted by the register 12a at a time are temporarily stored in the memory 21. When the frequency analyzer 23a has received the sampled data Da from the register 12a via the memory 21 (at Time t1), the frequency analyzer 23a initiates analysis of the frequencies of the sampled data Da (Data 1). When the storage (the HDD 22 in the embodiment) has received the sampled data Da from the register 12a via the memory 21 and the storage processing unit 23b (at Time t1), the storage initiates storage of Data 1. In the embodiment, the frequency analysis and storage of the plurality of the sampled data Da in the storage are completed by Time t2, which is before Time t3. In other words, the analysis period from initiation of analysis of the frequency of the sampled data Da (Data 1) to completion of the analysis (from Time t1 to Time t2) is shorter than the predetermined period (from Time t1 to Time t3). The storage period from initiation of the storage of the sampled data Da (Data 1) to completion of the storage is also shorter than the predetermined period (from Time t1 to Time t3). The arithmetic processing unit 2 is a hardware device that can achieve such operations. The analysis period and the storage period that are shorter than the predetermined period allow frequency analysis of all of the sampled data Da outputted from the sampler 12 at a time and allow storage of all of the sampled data Da in the storage. At time points after Time t1, such as Time t3, Time t5, and so on, the frequency analyzer 23a analyzes the frequencies of all of the sampled data Da (such as Data 2, Data 3, and so on) at intervals of the predetermined period, while the storage processing unit 23b stores all of the sampled data Da (such as Data 2, Data 3, and so on) on the HDD 22. The analysis period and the storage period for data such as Data 2, Data 3, and so on are also shorter than the predetermined period.

After the frequency analyzer 23a completes analysis of the frequencies of all of the sampled data Da (Data 1) at Time t2, the results of the frequency analysis are outputted from the frequency analyzer 23a to the abnormality determination unit 24 and the image generating unit 25. Then, the abnormality determination unit 24 initiates the abnormality determination, and the image generating unit 25 produces partial images 33 showing the results of the analysis of the frequencies of Data 1 for the respective sensors. The image generating unit 25 generates a partial image 32 (three-dimensional data image) showing the data in chronological order and in real time and an image for a display screen 31 and outputs the images to the display unit 3. When the result of the abnormality determination by the abnormality determination unit 24 is inputted to the image generating unit 25, the image generating unit 25 also uses the result of the abnormality determination to generate the image data for the display screen 31. Then, the display unit 3 displays the image data on the display screen 31. In the embodiment, the period required for the image generating unit 25 to generate the image data for the display screen 31 is longer than the predetermined period, and thus during generation of the image data for the display screen 31, a plurality of the frequency analysis processes may be completed, and a plurality of results of the frequency analysis processes may be provided. In this case, in the embodiment, the image generating unit 25 uses only the most current frequency analysis processes to generate the image data for the display screen 31. For example, in FIG. 3, generation of the image data for the display screen 31 by using the frequency analysis of Data 1 is completed at Time t7, which is later than Time t4, at which the frequency analysis of Data 2 is completed, and Time t6, at which the frequency analysis of Data 3 is completed. Thus, the data at Time t7 contains the results of the frequency analysis of Data 2 and the results of the frequency analysis of Data 3. In this case, the image generating unit 25 uses only the image data (partial images 33) for the results of the frequency analysis of Data 3, which is the most current result, to generate the image data for the display screen 31. Thus, at Time t7, the image generating unit 25 does not use the results of the frequency analysis of Data 2 but instead, uses the result for Data 3 to initiate generation of the image data for the display screen 31. Then, the display unit 3 displays the image data on the display screen 31. After Time t7, the abnormality determination unit 24 performs the abnormality determination, the image generating unit 25 generates image data for the display screen 31, and the display unit 3 displays the image data on the display screen 31 in the same manner.

Figure 4:
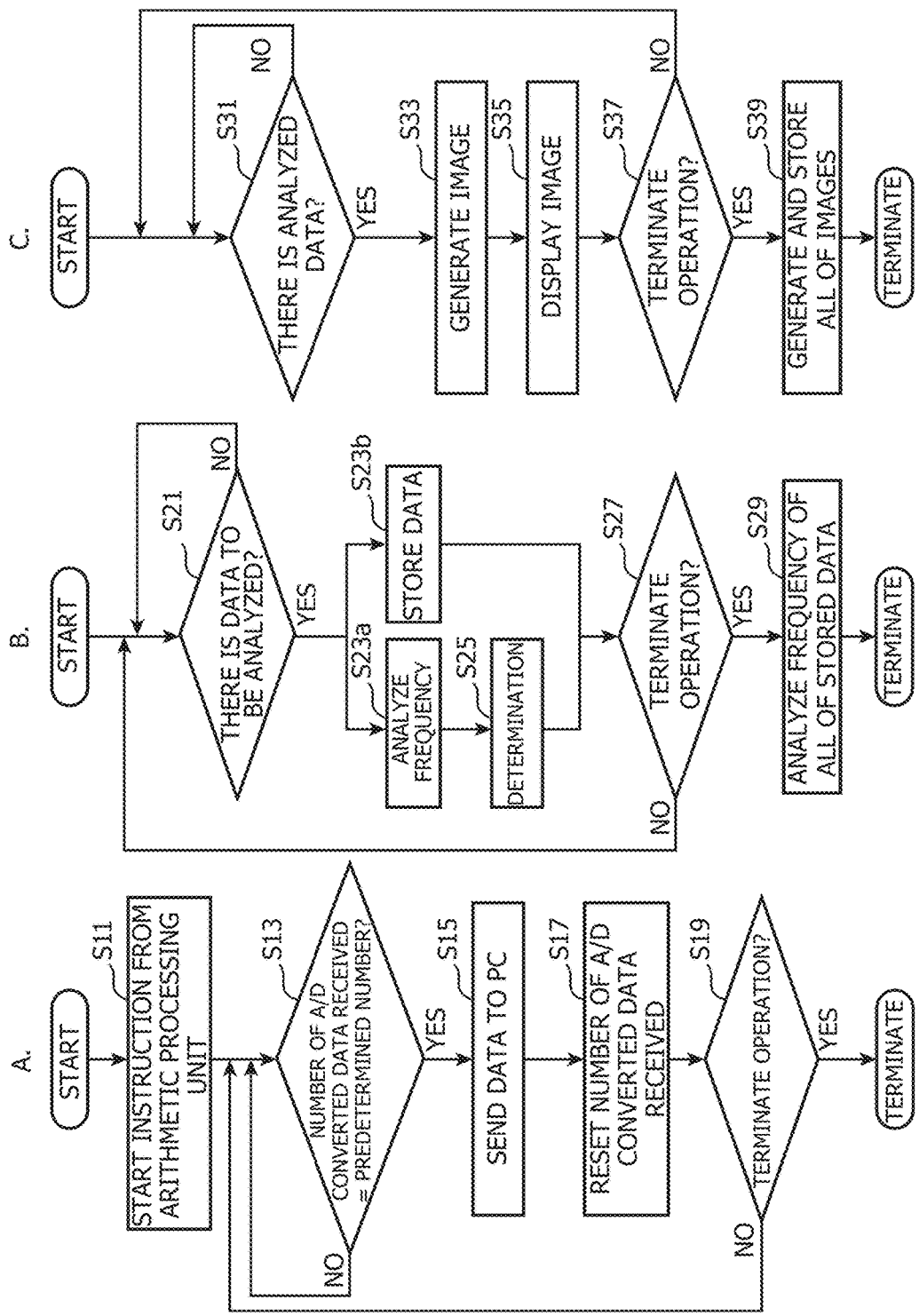
FIG. 4 is a flowchart illustrating the operations of a system for detecting an abnormality of rotating machines according to an embodiment of the present invention.

FIG. 4 is a flowchart illustrating the operations of the system 100 for detecting an abnormality of rotating machines according to the embodiment. FIG. 4A illustrates an operation flow of the sampler 12. FIG. 4B illustrates an operation flow of the frequency analyzer 23a, the storage processing unit 23b, and the abnormality determination unit 24. FIG. 4C illustrates an operation flow of the image generating unit 25 and the display unit 3. The operations illustrated in FIGS. 4A-4C are performed in parallel.

FIG. 4 illustrate a flow chart for one of the rotating machines 5 (for example, the rotating machine 5-1). The flow chart for the remaining rotating machines 5 (the rotating machines 5-2 to 5-n) is the same as in FIG. 4.

In FIG. 4A, first, the arithmetic processing unit 2 (the controller 23c) outputs an instruction to the sampler 12 to start sampling and A/D conversion of the signals transmitted by the transmitting unit 6. The sensors 10 detect vibration of the rotating machines 5, the amplifiers 11 amplify signals, the transmitting unit 6 transmits the signals to the sampler 12, and the sampler 12 samples and A/D-converts the transmitted signals and stores the sampled data Da in the register 12a (Step S11). From this point, the number of the sampled and A/D-converted data Da stored in the register 12a (hereinafter also referred to as "the number of the A/D-converted data received") begins increasing from zero. Then, the controller 23c determines whether the number of the A/D-converted data received has reached the predetermined number as described above (102,400 signals for the AE data and 65,536 signals for the acceleration data) (Step S13). If the number of data stored is smaller than the predetermined number (NO in Step S13), the determination in Step S13 is performed again, during which the sampled data Da are stored in the register 12a to increase the number of the A/D-converted data received. If the number of data stored has reached the predetermined number (YES in Step S13), all of the sampled data Da sent from the register 12a to the arithmetic processing unit 2 (the memory 21) within the predetermined period are outputted at a time (at intervals of the predetermined period) (Step S15). Then, the number of the A/D-converted data received is reset (Step S17), and the controller 23c determines whether the input unit (termination instruction input unit) 4 has received an instruction to terminate detection of abnormality from an operator (Step S19). If the input unit 4 has not received an instruction to terminate detection of abnormality from an operator (NO in Step S19), the operation flow goes back to Step S13 to repeat the operations such as the operation of outputting, at a time at intervals of a predetermined period, the plurality of the sampled data Da detected within the predetermined period in Step S15. If the input unit 4 has received an instruction to terminate detection of abnormality from an operator (YES in Step S19), the system 100 for detecting an abnormality performs a predetermined near-final process and then terminates detection of abnormality.

In FIG. 4B, first, the controller 23c determines whether all of the sampled data Da sent from the register 12a within the predetermined period, the data being for frequency analysis, are stored in the memory 21 (Step S21). If the controller 23c has determined that the data are not stored (NO in Step S21), the operation flow goes back to Step S21. If the controller 23c has determined that the data are stored (YES in Step S21), the frequency analyzer 23a analyzes the frequencies of all of the sampled data Da sent within the predetermined period at intervals of the predetermined period (for example, sufficient time intervals such as 1 sec to ascertain the tendency (trend) of the results of the frequency analysis) (Step S23a). In parallel, the storage processing unit 23b stores, on the HDD 22, all of the sampled data Da sent within the predetermined period (Step S23b). After the frequency analyzer 23a performs the frequency analysis, the abnormality determination unit 24 uses the results of the frequency analysis to determine presence of an abnormality of a component such as a rotor of the rotating machines 5 (Step S25). Then, the controller 23c determines whether the input unit (termination instruction input unit) 4 has received an instruction to terminate detection of abnormality from an operator (Step S27). If the input unit 4 has not received an instruction to terminate detection of abnormality from an operator (NO in Step S27), the operation flow goes back to Step S21. If the input unit 4 has received an instruction to terminate detection of abnormality from an operator (YES in Step S27), the system 100 for detecting an abnormality performs a predetermined near-final process and then terminates detection of abnormality. In the predetermined near-final process, the frequency analyzer 23a reads the sampled data Da at all of the time points from the HDD 22 to perform the frequency analysis and outputs the results of the frequency analysis to the image generating unit 25 (Step S29).

In FIG. 4C, first, the image generating unit 25 determines whether the data of the results of the frequency analysis have been inputted (Step S31). If the data of the result of frequency analysis has not been inputted (NO in Step S31), the operation flow goes back to Step S31. If the data of the results of the frequency analysis have been inputted (YES in Step S31), the image generating unit 25 generates the image data for the display screen 31 (Step S33) and outputs the image data to the display unit 3, which displays the image data (Step S35). If the result of abnormality determination by the abnormality determination unit 24 is inputted to the image generating unit 25, the image generating unit 25 also uses the result of the abnormality determination to generate the image data for the display screen 31. Then, the controller 23c determines whether the input unit 4 (termination instruction input unit 4a) has received an instruction to terminate detection of abnormality from an operator (Step S37). If the input unit 4 has not received an instruction to terminate detection of abnormality from an operator (NO in Step S37), the operation flow goes back to Step S31. If the input unit 4 has received an instruction to terminate detection of abnormality from an operator (YES in Step S37), the system 100 for detecting an abnormality performs a predetermined near-final process and then terminates detection of abnormality. In the predetermined near-final process, the image generating unit 25 receives the results of the frequency analysis (the amplitude data) at all of the time points by the frequency analyzer 23a, then generates the three-dimensional image data for the results of the frequency analysis (the amplitude data) at all of the time points, and transmits the image data to the HDD 22 (Step S39). The generation of the three-dimensional image data for the results of the frequency analysis at all of the time points in this manner and transmission of the image data to the the HDD 22 in the predetermined near-final process can result in a reduction in the processing load for storage on the HDD 22 via the controller 23c, compared with a case in which a result of the frequency analysis is stored on the HDD 22 every time a result of frequency analysis is provided during the frequency analysis.

In the system 100 for detecting an abnormality of rotating machines and the method for detecting an abnormality of rotating machines in the embodiment, the results of the frequency analysis of the sampled data that are created by sampling and detecting vibration of the respective n rotating machines 5-1 to 5-n are displayed in chronological order and in real time, and thus the operating states of the rotating machines 5 at respective times are displayed substantially in real time, which allows an operator to recognize a change in operation states of the rotating machines 5 over time, thereby allowing early detection of an abnormality of the rotating machines 5.

In the embodiment, the results of the frequency analysis and the results of the abnormality determination for the respective n rotating machines 5-1 to 5-n are displayed on the single display unit 3, which allows collective control of detection of an abnormality of the respective n rotating machines 5-1 to 5-n. Thus, the embodiment allows a reduction in the number of people who manage the process of detecting an abnormality of the n rotating machines 5-1 to 5-n.

Although the sampler 12 is disposed outside of the arithmetic processing unit 2 in the above embodiment, the sampler 12 may be disposed in the arithmetic processing unit 2. Although the input unit 4 receives an instruction to terminate detection of abnormality from an operator before storing, on the HDD 22, the image data that show the results of the frequency analysis and that are generated by the image generating unit 25 in the above embodiment, the frequency analyzer 23a may store the results of the frequency analysis on the HDD 22 every time the results of frequency analysis is provided (as shown by the dashed arrow in FIG. 1). In this case, after the frequency analyzer 23a receives a sampled data Da from the detecting unit 1 (via the memory 21), the frequency analyzer 23a may start storing the results of frequency analysis on the HDD 22. In the above embodiment, the control and arithmetic unit 23 may be configured to execute an abnormality detection program stored in ROM so that elements such as the abnormality determination unit 24 and the image generating unit 25 are functionally configured in the control and arithmetic unit 23.

Figure 5:
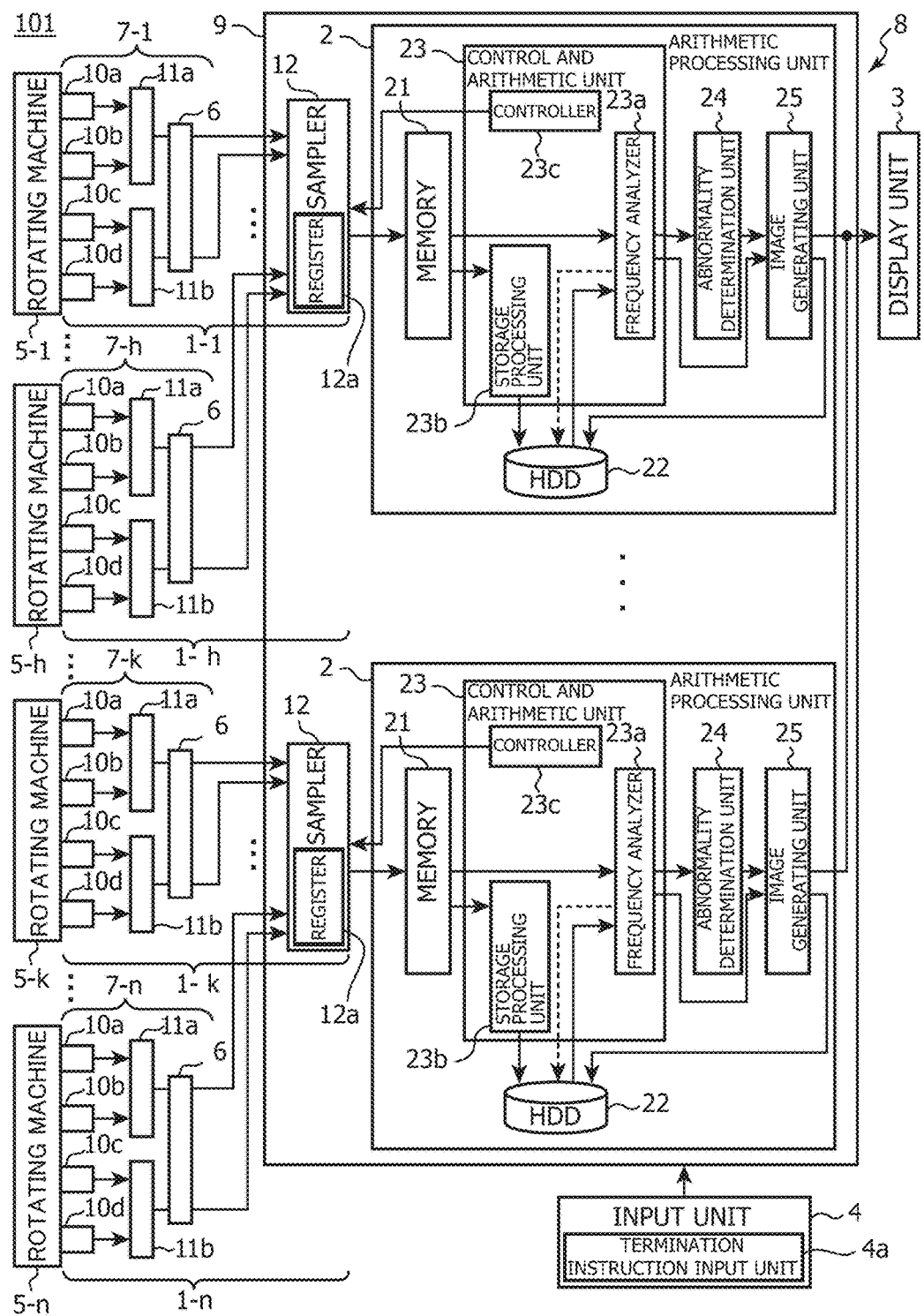
FIG. 5 is a block diagram illustrating an exemplary configuration of a system for detecting an abnormality of rotating machines according to a modified embodiment.

Now, a modification of the above embodiment will be described. FIG. 5 is a block diagram illustrating an exemplary configuration of a system 101 for detecting an abnormality of rotating machines according to the modification of the above embodiment. In the above embodiment, as illustrated in FIG. 1, the system includes a single pair of the arithmetic processing unit 2 and the sampler 12, and the pair performs frequency analysis for the respective n rotating machines 5-1 to 5-n. In the modification, the n rotating machines 5-1 to 5-n are divided into a plurality of groups (such as a group of the rotating machines 5-1 to 5-h . . . a group of the rotating machines 5-k to 5-n), and a single pair of the arithmetic processing unit 2 and the sampler 12 is allocated to each of the groups (1<h<k<n). Thus, in the system 101 for detecting an abnormality of rotating machines according to the modification, each of the pairs processes a smaller volume of data and thus can analyze frequency at higher speeds, compared with the system 100 for detecting an abnormality of rotating machines according to the embodiment.

What is claimed is:

1. A system for detecting an abnormality of rotating machines, the system comprising
two or more devices for detecting an abnormality of two or more rotating machines to which the devices are allocated respectively, and
a computer,
wherein the respective two or more devices for detecting an abnormality each comprise
a sensor for detecting vibration of a rotating machine to which the sensor is allocated and generating a signal indicative of the detected vibration, and
a transmitting unit for transmitting, to the computer, the signals generated by the sensor, and
wherein the computer comprises
a sampler for sampling and detecting, with a predetermined sampling frequency, the signals that are transmitted by the transmitting unit of the respective two or more devices for detecting an abnormality and that are indicative of the vibration and outputting, at a time at intervals of a predetermined period, a plurality of the sampled data detected within the predetermined period, a storage for storing the plurality of the sampled data that are outputted by the sampler and that correspond to the respective two or more rotating machines, a frequency analyzer for analyzing frequencies of the plurality of the sampled data that are outputted by the sampler and that correspond to the respective two or more rotating machines, an abnormality determination unit for determining whether the respective two or more rotating machines have an abnormality based on the results of the frequency analysis by the frequency analyzer, the results corresponding to the respective two or more rotating machines, and a display unit for displaying, in chronological order and in real time, the results of the frequency analysis, the results corresponding to the respective two or more rotating machines, and displaying the results of the determination, wherein the storage initiates storage of the plurality of the sampled data and the results of the frequency analysis when the storage has received the plurality of the sampled data from the detecting unit, and wherein the storage period from the initiation of the storage of the plurality of the sampled data to the end of the storage is shorter than the predetermined period.

2. The system for detecting an abnormality of rotating machines according to claim 1, wherein the frequency analyzer analyzes frequencies of the plurality of the sampled data by fast Fourier transform and outputs amplitude data corresponding to the respective frequencies.

3. The system for detecting an abnormality of rotating machines according to claim 2, wherein the display unit displays the results of the frequency analysis at respective times in chronological order, in real time, and in three dimensions: the frequency dimension, the amplitude dimension, and time dimension.

4. The system for detecting an abnormality of rotating machines according to claim 1, wherein the frequency analyzer initiates the frequency analysis when the frequency analyzer has received the plurality of the sampled data from the detecting unit, and wherein the analysis period from the initiation of the frequency analysis to the end of the frequency analysis is shorter than the predetermined period.

5. The system for detecting an abnormality of rotating machines according to claim 4, wherein the storage initiates storage of the plurality of the sampled data and the results of the frequency analysis when the storage has received the plurality of the sampled data from the detecting unit, and wherein the storage period from the initiation of the storage of the plurality of the sampled data to the end of the storage is shorter than the predetermined period.

6. The system for detecting an abnormality of rotating machines according to claim 4, wherein the system further comprises a termination instruction input unit for receiving an instruction to terminate detection of abnormality, wherein when the termination instruction input unit has received the instruction, the frequency analyzer reads all of the plurality of the sampled data stored in the storage, then analyzes the frequency of the data, and stores the results of the frequency analysis in chronological order in the storage.

7. The system for detecting an abnormality of rotating machines according to claim 5, wherein the frequency analyzer is functionally configured in a processor by executing a predetermined frequency-analysis-program, and wherein upon starting the frequency analysis, the frequency analyzer is functionally configured in the processor, while upon completing the frequency analysis, the frequency analyzer is cleared from the processor.

8. The system for detecting an abnormality of rotating machines according to claim 2, wherein the frequency analyzer initiates the frequency analysis when the frequency analyzer has received the plurality of the sampled data from the detecting unit, and wherein the analysis period from the initiation of the frequency analysis to the end of the frequency analysis is shorter than the predetermined period.

9. The system for detecting an abnormality of rotating machines according to claim 3, wherein the frequency analyzer initiates the frequency analysis when the frequency analyzer has received the plurality of the sampled data from the detecting unit, and wherein the analysis period from the initiation of the frequency analysis to the end of the frequency analysis is shorter than the predetermined period.

10. The system for detecting an abnormality of rotating machines according to claim 2, wherein the storage initiates storage of the plurality of the sampled data and the results of the frequency analysis when the storage has received the plurality of the sampled data from the detecting unit, and wherein the storage period from the initiation of the storage of the plurality of the sampled data to the end of the storage is shorter than the predetermined period.

11. The system for detecting an abnormality of rotating machines according to claim 3, wherein the storage initiates storage of the plurality of the sampled data and the results of the frequency analysis when the storage has received the plurality of the sampled data from the detecting unit, and wherein the storage period from the initiation of the storage of the plurality of the sampled data to the end of the storage is shorter than the predetermined period.

12. The system for detecting an abnormality of rotating machines according to claim 2, wherein the system further comprises a termination instruction input unit for receiving an instruction to terminate detection of abnormality, wherein when the termination instruction input unit has received the instruction, the frequency analyzer reads all of the plurality of the sampled data stored in the storage, then analyzes the frequency of the data, and stores the results of the frequency analysis in chronological order in the storage.

13. The system for detecting an abnormality of rotating machines according to claim 3, wherein the system further comprises a termination instruction input unit for receiving an instruction to terminate detection of abnormality, wherein when the termination instruction input unit has received the instruction, the frequency analyzer reads all of the plurality of the sampled data stored in the storage, then analyzes the frequency of the data, and stores the results of the frequency analysis in chronological order in the storage.

14. The system for detecting an abnormality of rotating machines according to claim 6, wherein the frequency analyzer is functionally configured in a processor by executing a predetermined frequency-analysis-program, and wherein upon starting the frequency analysis, the frequency analyzer is functionally configured in the processor, while upon completing the frequency analysis, the frequency analyzer is cleared from the processor.

15. The system for detecting an abnormality of rotating machines according to claim 1, wherein the frequency analyzer is functionally configured in a processor by executing a predetermined frequency-analysis-program, and wherein upon starting the frequency analysis, the frequency analyzer is functionally configured in the processor, while upon completing the frequency analysis, the frequency analyzer is cleared from the processor.

16. A system for detecting an abnormality of rotating machines, the system comprising
two or more devices for detecting an abnormality of two or more rotating machines to which the devices are allocated respectively, and
a computer,
wherein the respective two or more devices for detecting an abnormality each comprise
a sensor for detecting vibration of a rotating machine to which the sensor is allocated and generating a signal indicative of the detected vibration, and
a transmitting unit for transmitting, to the computer, the signals generated by the sensor, and
wherein the computer comprises
a sampler for sampling and detecting, with a predetermined sampling frequency, the signals that are transmitted by the transmitting unit of the respective two or more devices for detecting an abnormality and that are indicative of the vibration and outputting, at a time at intervals of a predetermined period, a plurality of the sampled data detected within the predetermined period,
a storage for storing the plurality of the sampled data that are outputted by the sampler and that correspond to the respective two or more rotating machines,
a frequency analyzer for analyzing frequencies of the plurality of the sampled data that are outputted by the sampler and that correspond to the respective two or more rotating machines,
an abnormality determination unit for determining whether the respective two or more rotating machines have an abnormality based on the results of the frequency analysis by the frequency analyzer, the results corresponding to the respective two or more rotating machines, and
a display unit for displaying, in chronological order and in real time, the results of the frequency analysis, the results corresponding to the respective two or more rotating machines, and displaying the results of the determination,
wherein the system further comprises a termination instruction input unit for receiving an instruction to terminate detection of abnormality,
wherein when the termination instruction input unit has received the instruction, the frequency analyzer reads all of the plurality of the sampled data stored in the storage, then analyzes the frequency of the data, and stores the results of the frequency analysis in chronological order in the storage.

17. The system for detecting an abnormality of rotating machines according to claim 16, wherein the frequency analyzer is functionally configured in a processor by executing a predetermined frequency-analysis-program, and wherein upon starting the frequency analysis, the frequency analyzer is functionally configured in the processor, while upon completing the frequency analysis, the frequency analyzer is cleared from the processor.

18. A method for detecting an abnormality of two or more rotating machines by using two or more devices for detecting an abnormality of the two or more rotating machines to which the devices are allocated respectively, the method comprising
a step of detecting vibration of the rotating machines to which the devices are allocated and generating signals indicative of the detected vibration by the respective two or more devices for detecting an abnormality,
a step of transmitting the signals generated in the generation step by the respective two or more devices for detecting an abnormality,
a step of sampling and detecting, with a predetermined sampling frequency, the signals that are transmitted in the transmission step by the respective two or more devices for detecting an abnormality and that are indicative of the vibration and outputting, at a time at intervals of a predetermined period, a plurality of the sampled data detected within the predetermined period,
a step of storing the plurality of the sampled data that are outputted in the sampling step and that correspond to the respective two or more rotating machines,
a step of analyzing frequencies of the plurality of the sampled data that are outputted in the sampling step and that correspond to the respective two or more rotating machines,
a step of determining whether the respective two or more rotating machines have an abnormality based on the results of the frequency analysis in the frequency analysis step, the results corresponding to the respective two or more rotating machines, and
a step of displaying, in chronological order and in real time, the results of the frequency analysis, the results corresponding to the respective two or more rotating machines, and displaying the results of the determination,
wherein in the storing step initiates storage of the plurality of the sampled data and the results of the frequency analysis when receiving the plurality of the sampled data from the detecting step, and
wherein the storage period from the initiation of the storage of the plurality of the sampled data to the end of the storage is shorter than the predetermined period.

* * * * *